(12) United States Patent
Chung et al.

(10) Patent No.: US 10,406,264 B2
(45) Date of Patent: Sep. 10, 2019

(54) PEPTIDE HAVING TITANIUM-BINDING ABILITY

(71) Applicants: NANO INTELLIGENT BIOMEDICAL ENGINEERING CORPORATION. CO. LTD, Chungcheongbuk-do (KR); SEOUL NATIONAL UNIVERSITY R&DB FOUNDATION, Seoul (KR)

(72) Inventors: Chong-Pyoung Chung, Seoul (KR); Yoon Jeong Park, Seoul (KR); Jue-Yeon Lee, Gyeonggi-do (KR); Yeonsu Kim, Seoul (KR); Dong Woo Lee, Seoul (KR)

(73) Assignees: NANO INTELLIGENT BIOMEDICAL ENGINEERING CORPORATION CO., LTD., Chungcheongbuk-Do (KR); Seoul National University R&DB Foundation, Seoul (KR)

( * ) Notice: Subject to any disclaimer, the term of this patent is extended or adjusted under 35 U.S.C. 154(b) by 62 days.

(21) Appl. No.: 15/545,679

(22) PCT Filed: Mar. 7, 2017

(86) PCT No.: PCT/KR2017/002436
§ 371 (c)(1),
(2) Date: Jul. 22, 2017

(87) PCT Pub. No.: WO2018/021647
PCT Pub. Date: Feb. 1, 2018

(65) Prior Publication Data
US 2018/0280577 A1 Oct. 4, 2018

(30) Foreign Application Priority Data
Jul. 26, 2016 (KR) ........................ 10-2016-0094893

(51) Int. Cl.
| | | |
|---|---|---|
| A61K 47/62 | (2017.01) | |
| A61L 27/54 | (2006.01) | |
| A61L 27/22 | (2006.01) | |
| C07K 14/51 | (2006.01) | |
| C07K 7/08 | (2006.01) | |
| A61K 47/18 | (2017.01) | |
| A61L 27/06 | (2006.01) | |
| C07K 17/14 | (2006.01) | |

(52) U.S. Cl.
CPC .............. *A61L 27/54* (2013.01); *A61K 47/18* (2013.01); *A61K 47/62* (2017.08); *A61L 27/06* (2013.01); *A61L 27/22* (2013.01); *A61L 27/227* (2013.01); *C07K 7/08* (2013.01); *C07K 14/51* (2013.01); *C07K 17/14* (2013.01); *A61L 2420/04* (2013.01); *A61L 2430/02* (2013.01); *A61L 2430/12* (2013.01); *C07K 2319/00* (2013.01)

(58) Field of Classification Search
CPC ............ A61K 8/29; A61K 47/62; A61L 27/54
See application file for complete search history.

(56) References Cited

U.S. PATENT DOCUMENTS

2015/0119334 A1* 4/2015 Rapaport ................ A61L 27/06
514/16.7

FOREIGN PATENT DOCUMENTS

| KR | 10-2012-0119706 A | 10/2012 |
|---|---|---|
| KR | 10-2016-0119580 A | 10/2016 |

OTHER PUBLICATIONS

Gnanasekar, M., et al., "Novel Phage Display-Based Subtractive Screening to Identify Vaccine Candidates of Brugia malayi", "Infection and Immunity", Aug. 2004, pp. 4707-4715, vol. 72, No. 8.
Yucesoy, D., et al., "Chimeric Peptides as Implant Functionalization Agents for Titanium Alloy Implants with Antimicrobial Properties", "JOM. Author Manuscript", 1989, pp. 1-28, vol. 67, No. 4.

* cited by examiner

*Primary Examiner* — Kaipeen E Yang
(74) *Attorney, Agent, or Firm* — Hultquist, PLLC; Steven J. Hultquist (57) ABSTRACT

The present invention relates to a peptide having the ability to bind specifically to the surface of titanium. The titanium-binding peptide according to the present invention is fixed securely to the titanium surface so that the activity of a physiologically active substance linked to the peptide can be stably maintained over a long period of time. Thus, the peptide can be effectively used for surgical regeneration therapy.

9 Claims, 8 Drawing Sheets
(2 of 8 Drawing Sheet(s) Filed in Color)
Specification includes a Sequence Listing.

PEPTIDE HAVING TITANIUM-BINDING ABILITY

CROSS-REFERENCE TO RELATED APPLICATIONS

This application is a U.S. national phase under the provisions of 35 U.S.C. § 371 of International Patent Application No. PCT/KR2017/002436 filed Mar. 7, 2017, which in turn claims priority of Korean Patent Application No. 10-2016-0094893 filed Jul. 26, 2016. The disclosures of such international patent application and Korean priority patent application are hereby incorporated herein by reference in their respective entireties, for all purposes.

TECHNICAL FIELD

The present invention relates to a titanium-binding peptide, and more particularly to a peptide having the ability to bind specifically to the surface of titanium, in which the peptide functions as a linker between titanium and a physiologically active substance to securely fix the physiologically active substance to the surface of titanium so as to enable the activity of the physiologically active substance to be maintained over a long period of time.

BACKGROUND ART

Dental implants are artificial teeth that replace missing teeth, and are widely used to enable the functional and aesthetic repair of missing teeth. In comparison to natural teeth attached to alveolar bone by periodontal ligament, dental implants are characterized in that artificial dental roots are attached directly to bone.

A dental implant is physically fixed by contact of the implant with the surrounding bone at the same time as placement and is biologically fixed by formation of new bone tissue around the implant and osseointegration with the surrounding bone after placement. However, in geriatric patients, it may be difficult to ensure initial stability, which is important in osseointegration, due to insufficient bone mass or reduced bone quality. In this case, early failure of implants may arise. Meanwhile, even in general adult patients in addition to geriatric patients having insufficient bone mass and reduced bone quality, the application of biological factors is essential for initial engraftment after implant placement and for shortening of the treatment period.

Materials for dental implants may be largely divided into metals, ceramics and polymers. These days, most dental implants are manufactured from commercially pure titanium (cpTi) or titanium alloys. At present, various methods for modifying the surface of implants are used to improve the interface between an implant made of titanium or its alloy and bone. In particular, studies have been conducted on the fifth generation implant technology in which biological or biochemical particles or components helpful in bone formation are added to a sandblasted, large-grit and acid-etched (SLA) surface in order to shorten the osseointegration period of implants. In addition, studies based on tissue engineering have been conducted on technologies in which growth factors such as proteins, which promote osteogenic responses, are attached to the surface of implants. In the case of implants made of apatite, studies on the use of apatite together with physiologically active proteins, such as extracellular matrix proteins, bone morphogenetic proteins or tissue growth factors, have been conducted. Furthermore, biomaterials and physiologically active substances have been used in combination, or products comprising a substance coated on the biomaterial surface, for example, GEM21S (containing PDGF) or INFUSE (containing BMP-2), have been developed and commercially used. However, in this case, there are problems in that, when these implants are placed in vivo, the physiologically active substance is easily released without being fixed securely to the biomaterial surface, and in severe cases, it is degraded by exposure to systemic blood, and thus the physiological activity thereof may be reduced and adverse effects in tissues other than a target tissue may arise. In addition, in the case of implants made of titanium or its alloy, various studies based on surface modification and physiologically active substances have been conducted, there are still problems in terms of stability, including possible surface peeling. Therefore, for tissue regeneration with implants, it is required that a physiologically active substance be fixed securely to the biomaterial surface so that the effective activity thereof can be maintained over a long period of time.

Accordingly, the present inventors have made extensive efforts to solve the above-described problems occurring in the prior art, and as a result, have identified a short peptide sequence having a strong binding affinity for the surface of an implant, and have found that the peptide easily binds to the surface of a titanium implant and is maintained in a stable state, thereby completing the present invention.

DISCLOSURE OF INVENTION

Technical Problem

It is an object of the present invention to provide a titanium-binding peptide represented by the amino acid sequence of SEQ ID NO: 1.

Another object of the present invention is to provide a peptide conjugate comprising a physiologically active peptide or protein linked to the titanium-binding peptide.

Still another object of the present invention is to provide a biomaterial comprising the titanium-binding peptide or the peptide conjugate.

Technical Solution

To achieve the above objects, the present invention provides a titanium-binding peptide represented by the amino acid sequence of SEQ ID NO: 1.

The present invention also provides a peptide conjugate comprising a physiologically active peptide or protein linked to the titanium-binding peptide.

The present invention also provides a biomaterial comprising the titanium-binding peptide or the peptide conjugate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In the present invention, in order to securely fix a physiologically active substance to enable the activity thereof to be maintained over a long period of time, by use of a peptide linker capable of binding to the surface of a titanium implant without chemical modification, a peptide sequence having a binding affinity for the surface of the titanium implant was identified by a phage display technique, and it was found that the peptide can be present on the titanium surface in a stably fixed state.

Therefore, in one aspect, the present invention is directed to a titanium-binding peptide represented by an amino acid sequence of SEQ ID NO: 1, the use of the titanium-binding peptide represented by an amino acid sequence of SEQ ID NO: 1, and a method of attaching a physiologically active substance to titanium using the peptide represented by an amino acid sequence of SEQ ID NO: 1.

In the present invention, the titanium-binding peptide preferably binds to titanium, which is used as a biomaterial, without chemical modification, but is not limited thereto.

In yet another aspect, the present invention is directed to a peptide conjugate comprising a physiologically active peptide or protein linked to the titanium-binding peptide. In a further aspect, the present invention is directed to the use of a peptide conjugate, comprising a physiologically active peptide or protein linked to the titanium-binding peptide, for improving physiological activity. In a still further aspect, the present invention is directed to a method of improving physiological activity using a peptide conjugate comprising a physiologically active peptide or protein linked to the titanium-binding peptide. For example, the improvement of the physiological activity may include the improvement of the bone regeneration ability, but is not limited thereto.

In the present invention, the conjugate of the titanium-binding peptide and the physiologically active peptide may be chemically synthesized using a peptide synthesizer. Specifically, a physiologically active domain may be sequentially chemically linked to the C- or N-terminus of the titanium-binding peptide, thereby synthesizing a titanium binding peptide-physiologically active peptide (e.g., osteogenic differentiation-inducing sequence) conjugate consisting of N terminus-titanium binding peptide-physiologically active domain-C terminus or N terminus-physiologically active domain-titanium binding peptide-C terminus.

The physiologically active peptide domain is a substance that has osteogenic differentiation-inducing activity or anti-inflammatory activity required for implant placement and that regulates gene expression and physiological function in vitro or in vivo. This physiologically active peptide domain may act as a controlling agent when a substance that is involved in functional regulation in vivo is deficient or when abnormal pathology caused by excessive secretion appears. It may be an L- or D-form in view of its stability in vivo.

In the present invention, the physiologically active peptide is preferably selected from the group consisting of anti-inflammatory, anti-microbial, cell adhesion, bone tissue regeneration, and cell migration functional peptides, but is not limited thereto.

In the present invention, the physiologically active protein is preferably selected from the group consisting of a tissue regeneration factor, a tissue growth factor, an intracellular transcription factor, an extracellular matrix protein, and an anti-inflammatory protein, but is not limited thereto.

In the present invention, a conjugate of the titanium-binding peptide with a physiologically active peptide or a low-molecular substance can be formed by inducing chemical bonding using a crosslinking agent. If chemical bonding is induced using a crosslinking agent, the conjugate will be easily formed by the crosslinking agent, because the N-terminus of the titanium-binding peptide has a free amino group.

Examples of a cross-linking agent that can be used in the present invention include, but not limited to, 1,4-bis-maleimidobutane (BMB), 1,11-bismaleimidotetraethyleneglycol (BM[PEO] 4), 1-ethyl-3-[3-dimethyl aminopropyl] carbodiimide hydrochloride (EDC), succinimidyl-4-[N-maleimidomethylcyclohexane-1-carboxy-[6-amidocaproate]] (SMCC) and its sulfonate (sulfo-SMCC), succinimidyl 6-[3-(2-pyridyldithio)-ropionamido] hexanoate (SPDP) and its sulfonate (sulfo-SPDP), m-maleimidobenzoyl-N-hydroxysuccinimide ester (MBS) and its sulfonate (sulfo-MBS), and succinimidyl [4-(p-maleimidophenyl) butyrate] (SMPB) and its sulfonate (sulfo-SMPB).

In the present invention, the peptide conjugate may be represented by the amino acid sequence of SEQ ID NO: 3 or 4, but is not limited thereto.

In the present invention, the titanium-binding peptide and the physiologically active protein or peptide may be linked to each other by a linker. The linker may be any linker that provides a space such that the titanium-binding peptide and the physiologically active protein or peptide can form a functional structure. For example, the linker may denote peptidic linkers of natural and/or synthetic origin. The peptidic linkers of natural and/or synthetic origin may have an amino acid chain consisting of 1 to 50 amino acids, and may contain repetitive amino acid sequences of naturally occurring polypeptides, such as polypeptides with a hinge-function. In another embodiment, the amino acid sequence of the peptidic linker may be a "synthetic peptidic linker amino acid sequence" that is designated to be rich in glycine, glutamine and/or serine residues. These residues are arranged e.g. in small repetitive units of up to five amino acids. This small repetitive unit may be repeated several times to form a multimeric unit. At the amino- and/or carboxy-terminal end of the multimeric unit, up to six additional arbitrary, naturally occurring amino acids may be added. Other synthetic peptidic linkers may be composed of a single amino acid that is repeated between 10 to 20 times. At each of the amino- and/or carboxy-terminal end, up to six additional arbitrary, naturally occurring amino acids may be present. Meanwhile, the linker may be a chemically modified form. For example, the linker may be used as a form of Fmoc-6-aminohexanoic acid (Fmoc-ε-Acp-OH) having the blocking group Fmoc-(9-fluorenylmethoxycarbonyl) coupled thereto, but is not limited thereto.

In yet further aspect, the present invention is directed to a biomaterial comprising the titanium-binding peptide or the peptide conjugate.

In the present invention, the biomaterial may be any one selected from the group consisting of a titanium-coated metal, a titanium-containing metal, a titanium-coated natural polymer, a natural polymer mixed with titanium, a titanium-coated synthetic polymer, a synthetic polymer mixed with titanium, and an implant for in vivo implantation made of titanium, but is not limited thereto.

As used herein, the term "implant" refers to a surgical material or procedure that is used to implant a biocompatible material into a defective area by an additional surgical operation such as bone grafting or distraction osteogenesis to thereby restore the function of the defective area. The defective area enters a regular regeneration stage after osseointegration that is the physiological, morphological and direct bonding of the placed implant body surface to the surrounding tissue whose normal function is maintained.

As used herein, the term "titanium" refers generally to commercially pure titanium (cpTi) or a titanium alloy. Titanium has a very high corrosion resistance, because a titanium oxide ($TiO_2$) film is naturally formed on the surface thereof. It is known that the titanium oxide film has a thickness of about 3-10 nm and that the presence of this film induces appropriate osseointegration. In addition, the titanium oxide film has an advantage in that it is stably and naturally formed even under unfavorable conditions such as intraoral conditions.

Titanium implants can be surface-modified in more diverse ways than zirconia ceramic implants that are currently used. For example, a sand-blasting technique is a processing method based on high-speed bombardment of fine sand particles, and the term "sand-blasting" is also used even when metal particles other than sand are used. For titanium, this technique is used to form a porous layer on the surface of titanium implants by bombarding titanium oxide with aluminum oxide particles. The adhesion of osteocytes to the surface of titanium implants can be increased by treating the surface by various surface modification methods. This can influence the initial stability of the implants.

In the present invention, the titanium is preferably an alloy obtained by adding 5-7 wt % of aluminum, 3-5 wt % of vanadium, 0-0.25 wt % of iron and 0-0.2 wt % of oxygen to pure titanium oxide, but is not limited thereto.

In the present invention, the natural polymer is preferably any one selected from the group consisting of collagen, alginic acid, propylene glycol, alginic acid, chondroitin sulfate, and chitosan, but is not limited thereto. In addition, the synthetic polymer is preferably any one selected from the group consisting of polylacticglycolic acid, poloxamer, and propylene glycol, but is not limited thereto.

When a titanium-coated metal, a titanium-containing metal, a titanium-coated natural polymer, a natural polymer mixed with titanium, a titanium-coated synthetic polymer, a synthetic polymer mixed with titanium, and an implant for in vivo implantation made of titanium are implanted in vivo, a physiologically active substance can be covalently bonded with the peptide without inducing chemical bonding so that it can be present in a stable state while the activity thereof can be maintained. Namely, the migration, proliferation and differentiation of bone tissue regeneration-associated cells around the implant will be promoted, and eventually an efficient tissue regeneration effect can occur within a short time so that the treatment time can be shortened. In addition, side effects on the whole body or other tissues, which can be induced due to an unstable bond on the implant surface, can be reduced. Thus, the implant is useful for surgical regenerative treatment.

In the present invention, a new phage display technique, named "subtractive panning", was additionally used to exclude the possibility of selecting a sequence that binds to materials other than the titanium disc surface.

As used herein, the term "subtractive panning" refers to a phage display technique which may be used to identify a sequence that binds to a specific material without binding to other specific materials. In the subtractive panning technique, a phage library is applied to a material that does not want to bind, and then only unbound phages are recovered, after which the phages are again applied to a material that wishes to bind, and then unbound phages are discarded, and only bound phages are recovered (Munirathinam, Gnanasekar et. al., Novel Phage Display-Based Subtractive Screening To Identify Vaccine Candidates of *Brugia malayi*, *Infect Immun.*, 72:4707-4715, 2004).

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Identification of Titanium-Binding Peptide Sequence by Phage Display

To identify a specific peptide sequence that binds to the titanium disc surface, a phage display technique was used. M13 phages labeled with a random peptide library with high diversity and complexity were applied to the titanium disc surface, after which unbound phages were washed out, and only bound phages were recovered. These procedures were repeated several times. A subtractive panning procedure was applied, and the DNA sequence encoding a peptide bound to the finally obtained phage was analyzed, thereby identifying a titanium-binding peptide sequence. The subtractive panning is a new phage display technique which may be used to identify a sequence that binds to a specific material without binding to other specific materials.

In this Example, polystyrene plate wells were used to identify a titanium-binding peptide through phage display, and thus this technique was applied to exclude sequences that bind not to the titanium disc surface but to the polystyrene plate.

More specifically, after completion of repeated cycles of the above-mentioned conventional phage display, the resulting phages were amplified again and added to empty wells of a polystyrene plate, and then phages not bound to the well surface were recovered. Then, the recovered phages not bound to the polystyrene plate were bound once more to the titanium disc surface, and then washed strongly with washing buffer, and only the remaining phages bound to the titanium disc surface were finally recovered.

The phage display kit used was Ph.D.-12 Phage Display Kit purchased from New England Biolabs (USA). 17 final clones screened using the kit phages labeled with a random peptide library consisting of 12 amino acids, provided by the kit were sent to Cosmogenetech Co., Ltd. (Korea) in an *E. coli* culture state to analyze the sequences thereof.

As a result, as can be seen in Table 1, it was shown that 14 clones had the same DNA sequence. A final peptide sequence (SLNYTGHRPVVH: SEQ ID NO: 1; Titanium Binding Peptide) composed of 12 amino acid residues could be obtained as TBP (titanium-binding sequence) by translating the DNA sequence. Since the peptide sequence is highly likely to be a sequence that binds specifically to the surface of titanium discs, the peptide sequence was selected as a candidate peptide sequence that binds specifically to the titanium disc surface. Among the remaining three clones, two clones were translated into peptide sequences composed of 8 amino acid residues, and one clone was translated into a peptide sequence composed of 12 amino acid residues, but this peptide sequence was excluded because a short linker sequence (3 amino acids) was identified as a sequence that could not be detected in the screening procedure performed using the kit.

TABLE 1

| Clone | DNA sequence | Amino acid sequence |
|---|---|---|
| #1 | 5'-TCT CTT AAT TAT ACG GGG CAT CGT CCG GTT GTG CAT-3' (SEQ ID NO: 9) | SLNYTGHRPVVH (SEQ ID NO: 1) |
| #2 | 5'-CAT AGT TAT AAG CAT CTT TTT GCT-5' (SEQ ID NO: 10) | HSYKHLFA (SEQ ID NO: 7) |
| #3 | 5'-TCT CTT AAT TAT ACG GGG CAT CGT CCG GTT GTG CAT-3' (SEQ ID NO: 9) | SLNYTGHRPVVH (SEQ ID NO: 1) |
| #4 | 5'-TCT CTT AAT TAT ACG GGG CAT CGT CCG GTT GTG CAT-3' (SEQ ID NO: 9) | SLNYTGHRPVVH (SEQ ID NO: 1) |
| #5 | 5'-TCT CTT AAT TAT ACG GGG CAT CGT CCG GTT GTG CAT-3' (SEQ ID NO: 9) | SLNYTGHRPVVH (SEQ ID NO: 1) |
| #6 | 5'-TCT CTT AAT TAT ACG GGG CAT CGT CCG GTT GTG CAT-3' (SEQ ID NO: 9) | SLNYTGHRPVVH (SEQ ID NO: 1) |
| #7 | 5'-TCT CTT AAT TAT ACG GGG CAT CGT CCG GTT GTG CAT-3' (SEQ ID NO: 9) | SLNYTGHRPVVH (SEQ ID NO: 1) |
| #8 | 5'-CAT AGT TAT AAG CAT CTT TTT GCT-5' (SEQ ID NO: 10) | HSYKHLFA (SEQ ID NO: 7) |
| #9 | 5'-TCT CTT AAT TAT ACG GGG CAT CGT CCG GTT GTG CAT-3' (SEQ ID NO: 9) | SLNYTGHRPVVH (SEQ ID NO: 1) |
| #10 | 5'-TCT CTT AAT TAT ACG GGG CAT CGT CCG GTT GTG CAT-3' (SEQ ID NO: 9) | SLNYTGHRPVVH (SEQ ID NO: 1) |
| #11 | 5'-TCT CTT AAT TAT ACG GGG CAT CGT CCG GTT GTG CAT-3' (SEQ ID NO: 9) | SLNYTGHRPVVH (SEQ ID NO: 1) |
| #12 | 5'-TCT CTT AAT TAT ACG GGG CAT CGT CCG GTT GTG CAT-3' (SEQ ID NO: 9) | SLNYTGHRPVVH (SEQ ID NO: 1) |
| #13 | 5'-TCT CTT AAT TAT ACG GGG CAT CGT CCG GTT GTG CAT-3' (SEQ ID NO: 9) | SLNYTGHRPVVH (SEQ ID NO: 1) |
| #14 | 5'-TCT CTT AAT TAT ACG GGG CAT CGT CCG GTT GTG CAT-3' (SEQ ID NO: 9) | SLNYTGHRPVVH (SEQ ID NO: 1) |
| #15 | 5'-TCT CTT AAT TAT ACG GGG CAT CGT CCG GTT GTG CAT-3' (SEQ ID NO: 9) | SLNYTGHRPVVH (SEQ ID NO: 1) |
| #16 | 5'-AAT ATT AAT TTT TCG TTT GGT CCG GTG ACT CAT ATT-3' (SEQ ID NO: 11) | NINFSFGPVTHI (SEQ ID NO: 8) |
| #17 | 5'-TCT CTT AAT TAT ACG GGG CAT CGT CCG GTT GTG CAT-3' (SEQ ID NO: 9) | SLNYTGHRPVVH (SEQ ID NO: 1) |

It was revealed that clone #16 had wrong short linker sequence (GRG) instead of correct sequence (GGG) which is not presented in this table.

Example 2: Synthesis of Titanium-Binding Peptides

Peptides of TBP (SLNYTGHRPVVH: SEQ ID NO: 1; Titanium Binding Peptide) or TBP-C (VSAAGTKASPAV; SEQ ID NO: 2; Titanium Binding Peptide-Control) were synthesized from the C-terminus to the N-terminus by an F-moc solid-phase synthesis method using a synthesizer. Specifically, the peptides were synthesized using Rink resin (0.075 mmol/g, 100~200 mesh, 1% DVB crosslinking) having Fmoc-(9-fluorenylmethoxycarbonyl) as a blocking group linked thereto. 50 mg of Rink resin was placed in a synthesizer, and then swollen with DMF, after which the Fmoc-group was removed using a 20% piperidine/DMF solution. A 0.5M amino acid solution (solvent: dimethylformamide, DMF) according to the sequence from the C-terminus to the N-terminus, 1.0M DIPEA (dimethylformamide & N-methylpyrrolidone, DMF & NMP) and 0.5M HBTU (solvent: dimethylformamide, DMF) were added to the resin in amounts of 5, 10 and 5 equivalents, respectively, and allowed to react for 1-2 hours under a nitrogen atmosphere. After completion of each of the deprotection and coupling steps, the resin was washed twice with DMF and NMP. Even after coupling of the final amino acid, the resin was deprotected to remove the Fmoc-group.

Synthesis of the peptides was confirmed using a ninhydrin test method. The tested and synthesized resin was dried with tetrahydrofuran (THF) or dichloromethane (DCM), and then a trifluoroacetic acid (TFA) cleavage cocktail was added to the resin in an amount of 20 ml per g of the resin, followed by shaking for 3 hours. Next, the cocktail containing the resin and peptide dissolved therein was separated by filtration. The filtered out solution was removed using a rotary evaporator. Then, cold ether was added, or an excess amount of cold ether was added directly to the TFA cocktail solution containing the peptide dissolved therein, so as to crystallize the peptide in a solid phase. The crystallized peptide was isolated by centrifugation. At this time, the TFA cocktail was completely removed by washing several times with ether and a centrifugation process. The peptides thus obtained were dissolved in distilled water and freeze-dried.

Each of the synthesized peptides was cut from the resin, washed, freeze-dried, and then purified by liquid chromatography. The molecular weights of the purified peptides were measured by mass spectrometry.

Comparative Example 1: Synthesis of TBP-C (VSAAGTKASPAV; SEQ ID NO: 2) Peptide

As a control for comparison with a titanium-binding peptide, a TBP-C(SLNATGARAVVA; SEQ ID NO: 2; Titanium Binding Peptide-Control) in which the histidine residues at positions 1 and 6, the proline residue at position 4 and the tyrosine residue at position 9 from the C-terminus in the sequence of SEQ ID NO: 1 are substituted with alanine was synthesized by an F-moc solid phase chemical synthesis method using a peptide synthesizer.

Comparative Example 2: Synthesis of Zirconia-Binding Peptide

As a control for comparison with a titanium-binding peptide, a zirconia-binding peptide (VSPFGTKWSPFV; SEQ ID NO: 5, Korean Patent Application No. 10-2015-0048441), which is a patented sequence possessed by the applicant, was synthesized by an F-moc solid phase chemical synthesis method using a peptide synthesizer.

Comparative Example 3: Synthesis of Osteogenic Peptide Linked to Titanium-Binding Peptide For evaluation of performance, a sequence comprising an osteogenic peptide (GLRSKSKKFRRPDIQYPDA; SEQ ID NO: 6, Korean Patent Application No. 10-2011-0037839) (which is a patented sequence possessed by the applicant) linked to a titanium-binding peptide was synthesized by an F-moc solid phase chemical synthesis method using a peptide synthesizer.

Comparative Example 4: Synthesis of Osteogenic Peptide Linked to Titanium-Binding Peptide by Linker For evaluation of performance, a sequence comprising an osteogenic peptide (GLRSKSKKFRRPDIQYPDA; SEQ ID NO: 6, Korean Patent Application No. 10-2011-0037839) (which is a patented sequence possessed by the applicant) linked to a titanium-binding peptide (SLNYTGHRPVVH Linker GLRSKSKKFRRPDIQYPDA; SEQ ID NO: 4) by a linker was synthesized by an F-moc solid phase chemical synthesis method using a peptide synthesizer. As the linker, Fmoc-6-aminohexanoic acid (Fmoc-ε-Acp-OH) having the blocking group Fmoc-(9-fluorenylmethoxycarbonyl) coupled thereto was used. The osteogenic peptide, the linker and the titanium-binding peptide were sequentially synthesized from the C-terminus to the N-terminus.

Comparative Example 5: Synthesis of Osteogenic Peptide

As a control for comparison with a titanium-binding peptide, an osteogenic peptide (GLRSKSKKFRRP-DIQYPDA; SEQ ID NO: 6, Korean Patent Application No. 10-2011-0037839), which is a patented sequence possessed by the applicant, was synthesized by an F-moc solid phase chemical synthesis method using a peptide synthesizer.

Example 3: Analysis of the Binding Affinity of Titanium-Binding Peptide for Titanium 3-1: Synthesis of Titanium-Binding Peptide Labeled with Biotin In order to examine the binding affinities of the peptides synthesized in Example 1 and Comparative Examples 1 and 2 for titanium, the peptides were labeled with biotin. Each of the peptides was biotinylated using EZ-Link Sulfo-NHS-Biotin (Pierce Biotechnology, USA) according to the manufacturer's instruction, and unbound byproducts were removed by ultrafiltration that is a membrane separation method based on a pressure difference. The molecular weights of the synthesized products were measured by mass spectrometry. The synthesized products were analyzed and purified by reverse phase liquid chromatography. For analysis, a $C_{18}$ column having a diameter of 4.6 mm was used, and 0.1% TFA/$H_2O$ and 0.092% TFA/acetonitrile were flushed onto the column at a rate of 1 ml/min with a gradient of 0-60% for 30 minutes. The wavelength of the UV detector used was 220 nm. For purification, a column having a diameter of 2.2 cm was used, and a flow rate of 20 ml/min and the solvent and detection wavelength as described above were used. Only the biotin-labeled peptide fraction was collected, and concentrated using a rotary evaporator to remove the solvent, followed by freeze-drying.

3-2: Measurement of Binding Affinity of Titanium-Binding Peptide for Titanium

The binding affinity of the titanium-binding peptide for titanium was measured by performing a binding assay using an avidin-biotin complex. Specifically, one titanium disc was placed in each well of a 24-well polystyrene plate, and then blocked with a blocking buffer (0.1 M $NaHCO_3$ (pH 8.6), 5 mg/ml BSA, 0.02% $NaN_3$ (optional), filter sterilize) for at least one hour. Next, the blocking buffer was discarded, and each titanium disc was strongly washed six times or more with a washing buffer (TBS+0.1% [v/v] Tween-20), after which 50 μl of each of the titanium-binding peptide TBP (SEQ ID NO: 1) of Example 1 and the peptides TBP-C(SEQ ID NO: 2) and ZBP (SEQ ID NO: 5, Korean Patent Application No. 10-2015-0048441) of Comparative Examples 1 and 2, which were biotin-labeled, synthesized, separated and purified in Example 3-1, was dispensed to the surface of each titanium disc at a concentration ranging from 100 nM to 1 μM. Each titanium disc was incubated at room temperature for 15 hours, and then washed strongly six times or more with a washing buffer, and 50 μl of a 1:500 dilution of ExtrAvidin-peroxidase (2,2'-AZINO-BIS, Cat. #A3219, Sigma-Aldrich, USA) in a blocking buffer was dispensed to the surface of each titanium disc. Each titanium disc was incubated at room temperature for 1 hour, and then washed strongly six times or more with a washing buffer, after which 50 μl of a substrate solution (2,2'-AZINO-BIS, Cat. #A3219, Sigma-Aldrich, USA) was dispensed to the surface of each titanium disc and allowed to react at room temperature for 20 minutes so as to develop color. Each titanium disc was treated with 50 μl of 1% SDS solution to stop the reaction, and the absorbance at 405 nm was measured.

Figure 1:
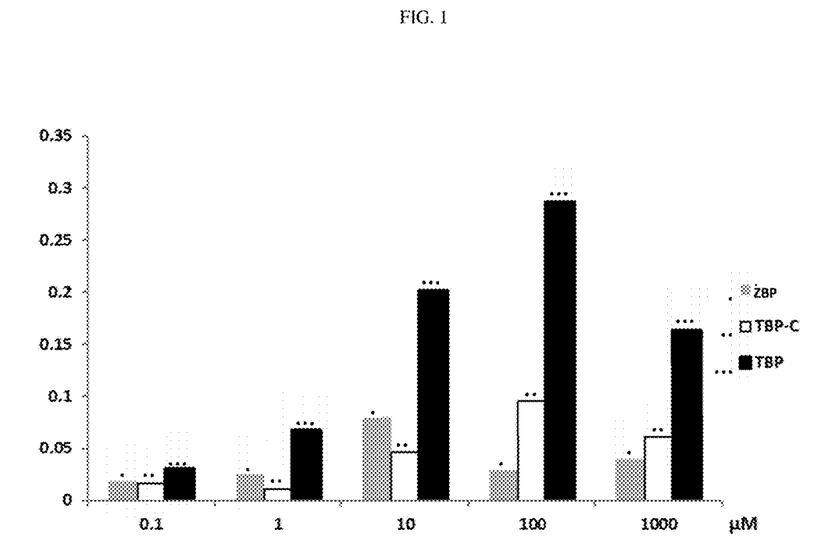
FIG. 1 shows the results of a binding assay performed using an avidin-biotin complex in order to examine the binding affinities of a titanium-binding peptide (SEQ ID NO: 1), a control TBP-C peptide (SEQ ID NO: 2) and a control zirconia-binding peptide (SEQ ID NO: 5) for titanium.

As a result, as can be seen in FIG. 1, when each titanium disc was treated with each of the titanium-binding peptide TBP (SEQ ID NO: 1) of Example 1, the peptide TBP-C(SEQ ID NO: 2) of Comparative Example 1, and the peptide ZBP (SEQ ID NO: 5, Korean Patent Application No. 10-2015-0048441) of Comparative Example 2, the absorbance value of the titanium-binding peptide TBP of Example 1 was higher than that of the peptides TBP-C and ZBP of Comparative Examples 1 and 2, and this increase in absorbance value was concentration-dependent. This demonstrates that the titanium-binding peptide sequence is a sequence that binds to the titanium disc surface in a concentration-dependent manner. In addition, such results suggest that the peptide sequence has a binding motif. In addition, the absorbance values of the peptides TBP-C and ZBP of Comparative Examples 1 and 2 were lower than that of titanium-binding peptide TBP of Example 1, and the peptides TBP-C and ZBP of Comparative Examples 1 and 2 showed the absorbance values independent of the concentration thereof, indicating that the peptide sequences of TBP-C and ZBP of Comparative Examples 1 and 2 do not bind to the titanium disc surface.

Figure 2:
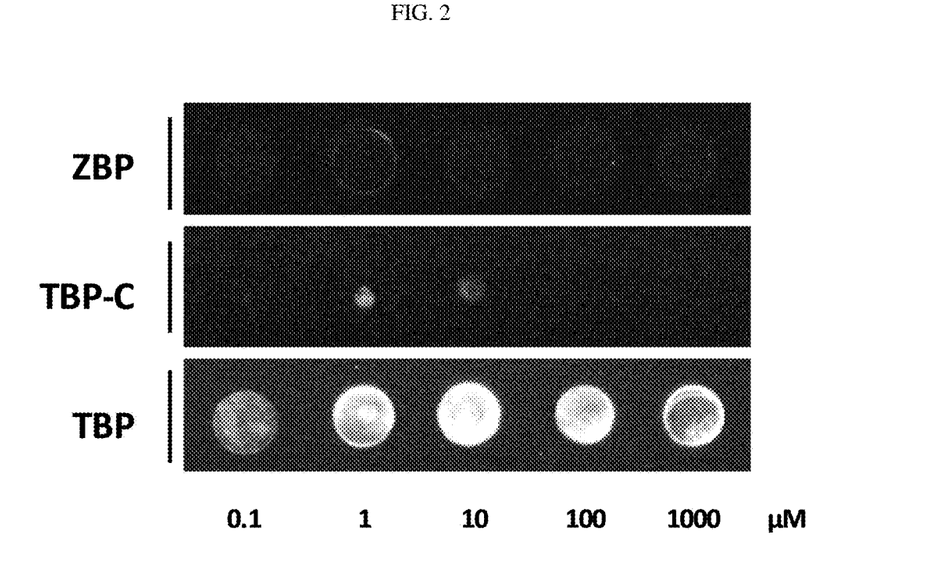
FIG. 2 shows the results of a luminescent image analysis performed using enhanced chemiluminescence (ECL) solution as a substituted substrate to visually demonstrate the results of the binding assay using Avidin-Biotin Complex in order to examine the binding affinities of a titanium-binding peptide (SEQ ID NO: 1), a control TBP-C peptide (SEQ ID NO: 2) and a control zirconia-binding peptide (SEQ ID NO: 5) for titanium.

In order to visually demonstrate measurement results, detection was performed using a luminescent image analyzer (LAS-1000, Fujifilm, Japan). Specifically, washing was performed at least three times with suitable washing solution to remove 2,2'-AZINO-BIS used as a substrate in the above procedure, and then analysis was performed with a luminescent image analyzer using enhanced chemiluminescence (ECL) solution. As a result, as can be seen in FIG. 2, only the peptide bound to the titanium disc was detected. This demonstrates that the titanium-binding peptide (TBP) of Example 1 binds to a titanium disc, whereas the TBP-C and ZBP synthesized in Comparative Examples 1 and 2 hardly bind to a titanium disc.

Example 4: Examination of Maximum Binding Amount of Titanium-Binding Peptide

To examine the maximum binding amount of the titanium-binding peptide TBP (SEQ ID NO: 1) per unit area of the titanium disc surface, a binding assay using an avidin-biotin complex was performed. Specifically, one titanium disc was placed in each well of a 24-well polystyrene plate, and then blocked with a blocking buffer (0.1 M NaHCO$_3$ (pH 8.6), 5 mg/ml BSA, 0.02% NaN$_3$ (optional), filter sterilize) for at least one hour. Next, the blocking buffer was discarded, and each titanium disc was strongly washed six times or more with a washing buffer (TBS+0.1% [v/v] Tween-20), after which 50 μl of each of the titanium-binding peptide TBP (SEQ ID NO: 1) of Example 1 and the peptides TBP-C(SEQ ID NO: 2) and ZBP (SEQ ID NO: 5, Korean Patent Application No. 10-2015-0048441) of Comparative Examples 1 and 2, which were biotin-labeled, synthesized, separated and purified in Example 3-1, was dispensed to the surface of each titanium disc at a concentration ranging from 100 nM to 40 mM. Each titanium disc was incubated at room temperature for 15 hours, and then washed strongly with a washing buffer, and 50 μl of a 1:500 dilution of ExtrAvidin-peroxidase (Cat. #E2886, Sigma-Aldrich, USA) in a blocking buffer was dispensed to the surface of each titanium disc. Each titanium disc was incubated at room temperature for 1 hour, and then washed strongly with a washing buffer, after which 50 μl of a substrate solution (2,2'-AZINO-BIS, Cat. #A3219, Sigma-Aldrich, USA) was dispensed to the surface of each titanium disc and allowed to react at room temperature for 20 minutes so as to develop color. Each titanium disc was treated with 50 μl of 1% SDS solution to stop the reaction, and the absorbance at 405 nm was measured.

Figure 3:
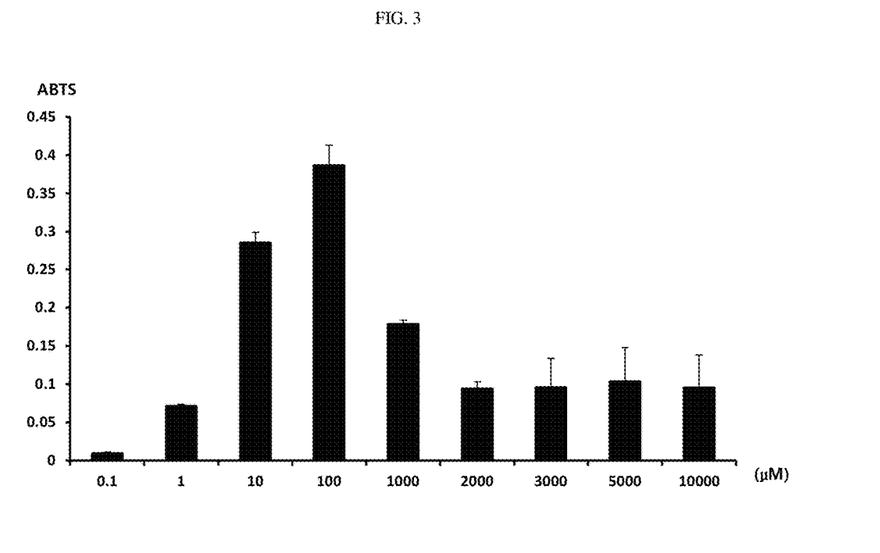
FIG. 3 shows the results of a binding assay performed using an avidin-biotin complex in order to determine the maximum binding of a titanium-binding peptide (SEQ ID NO: 1) to the surface of a titanium disc.
Figure 4:
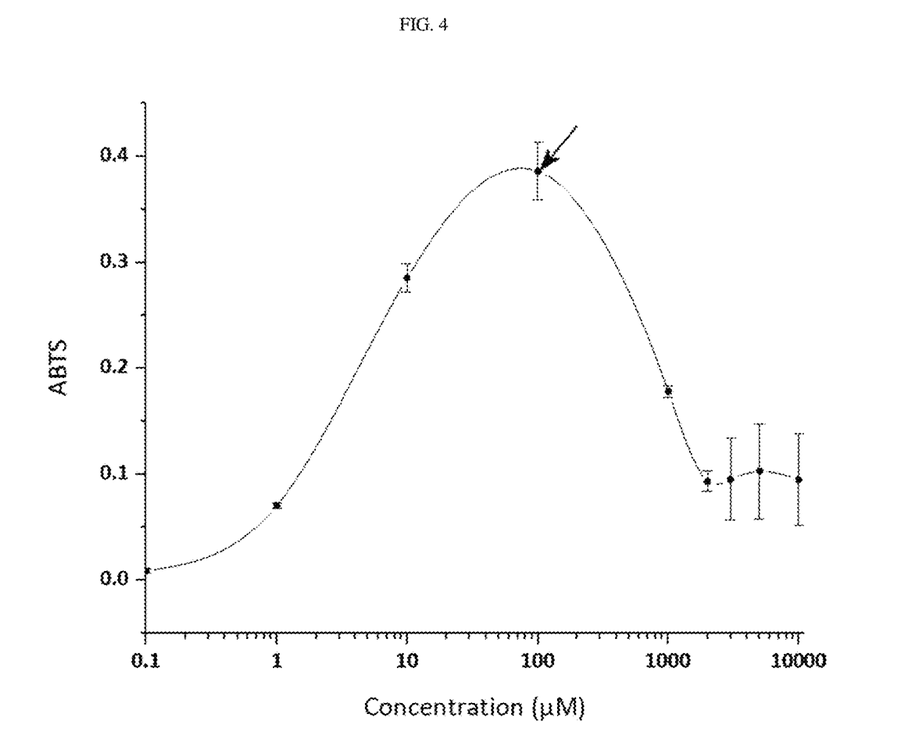
FIG. 4 shows the results of expressing the X-axis of FIG. 3 in log scale.

As a result, as can be seen in FIGS. 3 and 4, the titanium-binding peptide TBP (SEQ ID NO: 1) showed the maximum absorbance value at a concentration of 100 μM. Based on the back-calculation from the molecular weight and dispensing amount of the titanium-binding peptide, it can be seen that the maximum amount of titanium-binding peptide bound to the surface of one titanium disc is 8.025 μg. Thus, it can be seen that, because the diameter of the titanium disc is 10 mm, about 0.10223 μg of the titanium-binding peptide can be fixed per mm$^2$ of the titanium disc surface.

Example 5: In Vitro Evaluation of Cytotoxicity of Osteogenic Peptide Linked to Titanium-Binding Peptide In order to evaluate whether or not a titanium binding peptide-linked osteogenic peptide (SEQ ID NO: 3 or SEQ ID NO: 4) and a titanium-binding peptide (SEQ ID NO: 1) are cytotoxic when these peptides are administered alone, a cell viability test was performed.

Specifically, one titanium disc was placed in each well of a 24-well low-attachment polystyrene plate and blocked with a blocking solution (0.1 M NaHCO$_3$ (pH 8.6), 5 mg/ml BSA, 0.02% NaN$_3$ (optional), filter sterilize) for at least 1 hour. Next, the blocking solution was discarded, and each well was washed three times or more with a washing solution (DPBS: Dulbeccos phosphate buffered saline), after which 50 μl of the solution shown in Table 2 below was dispensed and coated on the surface of each titanium disc. Each well was incubated at room temperature for 15 hours, and then washed three times or more with a washing solution (DPBS). Next, 3×10$^4$ PDLSC cells suspended in 50 μl of a medium (Minimum Essential Medium Eagle Alpha Modifications, Hyclone, USA) containing 10% FBS (Fetal Bovine Serum) and 1% antibiotic-antimycotic solution (Thermo Fisher Scientific, USA) were dispensed per titanium disc. After at least 7 hours, the cells were observed to be attached to the disc surface, and the medium was additionally added to each well so that the disc would be submerged in the medium, followed by culture of the cells for 3 days. Next, the cells were detached, stained with trypan blue, and counted with a hematocytometer to determine the number of viable cells.

TABLE 2

| Physiologically active substance | Negative control | TBP | TBP-osteogenic peptide | TBP-Linker-osteogenic peptide | Osteogenic peptide | BMP-2 |
|---|---|---|---|---|---|---|
| Concentration | x | 100 μM | 100 μM | 100 μM | 100 μM | 100 ng/ml |

Figure 5:
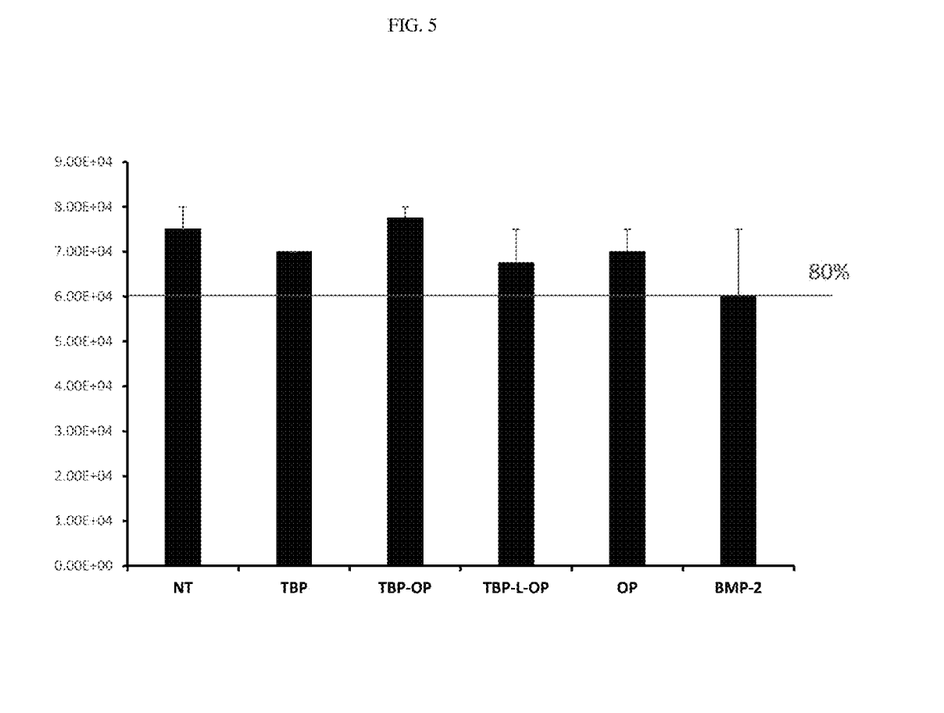
FIG. 5 shows the results of a cell viability test performed to evaluate the cytotoxicities of a titanium-binding peptide (SEQ ID NO: 1), an osteogenic peptide linked to a titanium-binding peptide (SEQ ID NO: 3 or SEQ ID NO: 4), and an osteogenic peptide (SEQ ID NO: 6) upon administration of these peptides.

As a result, the number of viable cells is as shown in Table 3 below. The cell viability on the titanium binding peptide-linked osteogenic peptide or the titanium-binding peptide was compared with that on the negative control, and the results are shown in FIG. 5. The results in FIG. 5 demonstrated that, when the titanium binding peptide-linked osteogenic peptide (SEQ ID NO: 3 or 4) or the titanium-binding peptide (SEQ ID NO: 1) was administered alone, it was not cytotoxic for cells during 3 days of incubation.

TABLE 3

| Total cell number | NT negative control | TBP | TBP-osteogenic peptide | TBP-Linker-osteogenic peptide | Osteogenic peptide | BMP-2 |
|---|---|---|---|---|---|---|
| #1 | $8.0 \times 10^4$ | $7.0 \times 10^4$ | $7.5 \times 10^4$ | $6.0 \times 10^4$ | $7.5 \times 10^4$ | $4.5 \times 10^4$ |
| #2 | $7.0 \times 10^4$ | $7.0 \times 10^4$ | $8.0 \times 10^4$ | $7.5 \times 10^4$ | $6.5 \times 10^4$ | $7.5 \times 10^4$ |
| Average | $7.5 \times 10^4$ | $7.0 \times 10^4$ | $7.8 \times 10^4$ | $6.8 \times 10^4$ | $7.0 \times 10^4$ | $6.0 \times 10^4$ |
| SD | $5.0 \times 10^3$ | — | $2.5 \times 10^3$ | $7.5 \times 10^3$ | $5.0 \times 10^3$ | $1.5 \times 10^4$ |

Example 6: In Vitro Evaluation of Function of Osteogenic Peptide Linked to Titanium-Binding Peptide 6-1: Measurement of Alkaline Phosphatase (ALP) Activity of Osteogenic Peptide Linked to Titanium-Binding Peptide In order to examine the osteogenic differentiation-inducting activity and loading of a titanium binding peptide-linked osteogenic peptide (SEQ ID NO: 3 or SEQ ID NO: 4) and a titanium-binding peptide (SEQ ID NO: 1) when these peptides are administered once, evaluation of ALP activity in periodontal ligament stem cells (PDLSCs) was performed. Specifically, one titanium disc was placed in each well of a 24-well low-attachment polystyrene plate and blocked with a blocking solution (0.1 M $NaHCO_3$ (pH 8.6), 5 mg/ml BSA, 0.02% $NaN_3$ (optional), filter sterilize) for at least 1 hour. Next, the blocking was discarded, and each well was washed three times or more with a washing solution solution (DPBS: Dulbeccos phosphate buffered saline), after which 50 µl of the solution shown in Table 2 of Example 5 was dispensed and coated on the surface of each titanium disc. Each well was incubated at room temperature for 15 hours, and then washed three times or more with a washing solution (DPBS). Next, $3 \times 10^4$ PDLSC cells suspended in 50 µl of a medium (Minimum Essential Medium Eagle Alpha Modifications, Hyclone, USA) containing 10% FBS (Fetal Bovine Serum) and 1% antibiotic-antimycotic solution (Thermo Fisher Scientific, USA) were dispensed per titanium disc. After at least 7 hours, the cells were observed to be attached to the disc surface, and the medium was additionally added to each well so that the disc would be submerged in the medium, followed by culture of the cells. On the next day, the medium was replaced with an osteogenic differentiation induction medium (Differentiation Basal Medium-Osteogenic, Lonza, USA) containing a supplement (hMSC Osteogenic SingleQuots®, Lonza, USA), and the cells were cultured for 18 days.

For 18 days after the first coating of the disc surface, the cells were cultured while replacing the medium without adding a solution containing the physiologically active substance. On day 0, 6, 10, 13 and 18 of culture, cultured media were recovered, and ALP activity was measured using an alkaline phosphatase assay kit (cat#.ab83369, abcam, USA).

Figure 6:
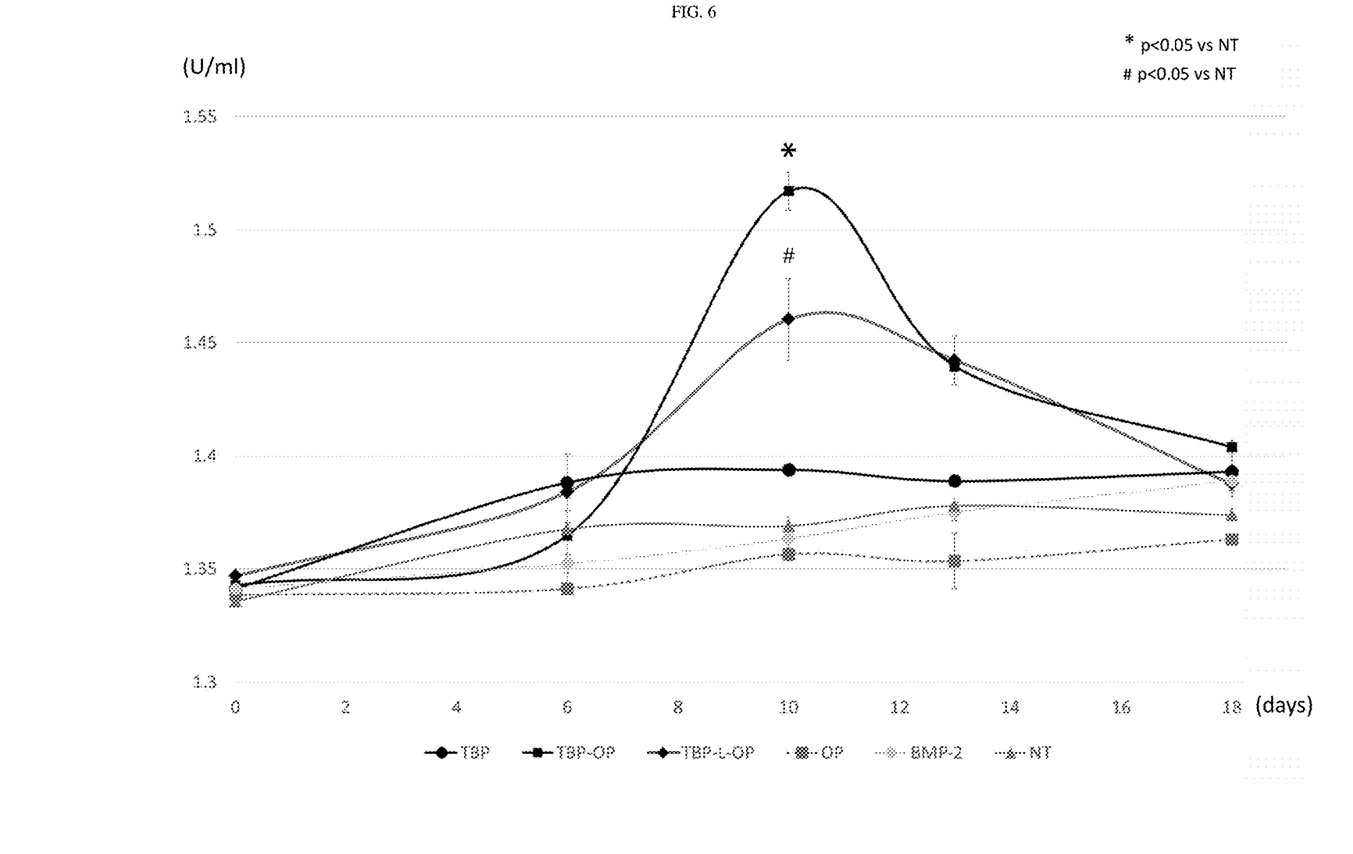
FIG. 6 shows the results of evaluating ALP activity in periodontal ligament stem cells (PDLSCs) for 18 days in order to examine the osteogenic differentiation-inducting activity and loading of each of a titanium-binding peptide (SEQ ID NO: 1), an osteogenic peptide linked to a titanium-binding peptide (SEQ ID NO: 3 or SEQ ID NO: 4), and an osteogenic peptide (SEQ ID NO: 6) when these peptides are administered once.
Figure 7:
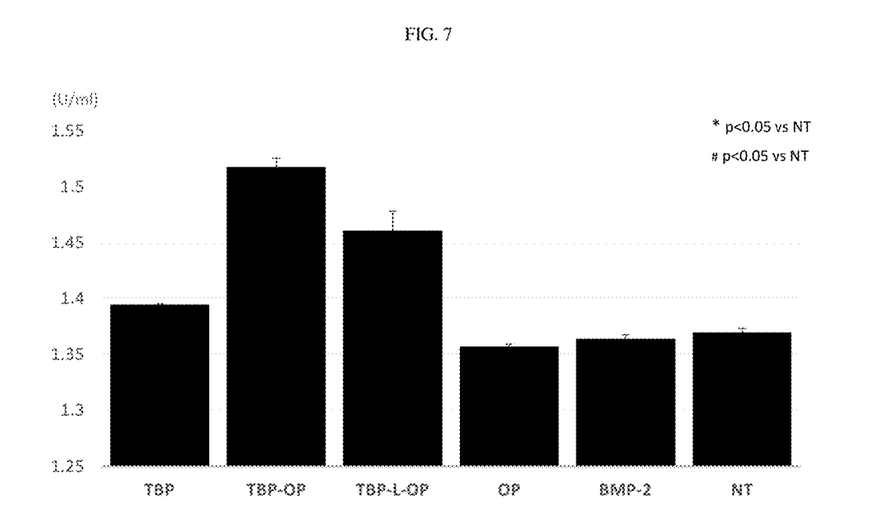
FIG. 7 shows ALP activity on day 10 of culture in the results shown in FIG. 6.

As a result, as can be seen in FIG. 6, a significant change in ALP activity was not observed in the test group treated with the osteogenic peptide (Comparative Example 5; SEQ ID NO: 6) linked to the titanium binding peptide and the control group treated with BMP-2 (bone morphogenetic protein). When repeated two-way ANOVA was performed in order to examine significance depending on the culture time and the kind of treating substance, it was shown that ALP activity did differ depending on the culture time and the kind of treating substance, and that the culture time and the treating substance had an interacting effect ($p<0.05$). In addition, in order to examine whether or not the difference in ALP activity between the treating substances on day 10 of culture is statistically significance, the results of measurement of ALP activity on day 10 of culture were analyzed. As shown in FIG. 7, on day 10 of culture, there was a statistically significant difference between the NT (negative control) group and the test group treated with the titanium binding peptide-linked osteogenic peptide (Comparative Example 3; SEQ ID NO: 3) and between the NT group and the test group treated with the osteogenic peptide linked to the titanium binding peptide by the linker (Comparative Example 4; SEQ ID NO: 4) ($p<0.05$). Furthermore, the results of the t-test indicated that there was no statistically significant difference between the test group treated with the titanium binding peptide-linked osteogenic peptide (Comparative Example 3; SEQ ID NO: 3) and the test group treated with the osteogenic peptide linked to the titanium binding peptide by the linker (Comparative Example 4; SEQ ID NO: 4) ($p>0.05$). In addition, the results of one-way ANOVA indicated that there was no statistically significant difference between the negative control group, the control group treated with BMP-2, and the test group treated with the bond-regenerating peptide (Comparative Example 5; SEQ ID NO: 6) alone ($p>0.05$).

In conclusion, only the osteogenic peptide linked to the titanium-binding peptide (TBP) of Example 1, such as the peptides synthesized in Comparative Examples 3 and 4, showed a statistically significant change in ALP activity during 18 days of culture. However, the physiologically active substances not linked to the titanium-binding peptide showed no significant change in ALP activity.

6-2: Evaluation of Mineralization-Inducing Activity of Osteogenic Peptide Linked to Titanium-Binding Peptide In order to examine the osteogenic differentiation-inducting activity and loading of a titanium binding peptide-linked osteogenic peptide (SEQ ID NO: 3 or SEQ ID NO: 4) when being administered once, mineralization of periodontal ligament stem cells (PDLSCs) by the peptide was evaluated. Specifically, one titanium disc was placed in each well of a 24-well low-attachment polystyrene plate and blocked with a blocking solution (0.1 M $NaHCO_3$ (pH 8.6), 5 mg/ml BSA, 0.02% $NaN_3$ (optional), filter sterilize) for at least 1 hour. Next, the blocking solution was discarded, and each well was washed three times or more with a washing solution (DPBS: Dulbeccos phosphate buffered saline), after which 50 µl of the solution shown in Table 2 of Example 5 was dispensed and coated on the surface of each titanium disc. Each well was incubated at room temperature for 15 hours, and then washed three times or more with a washing solution (DPBS). Next, 3×10⁴ PDLSC cells suspended in 50 µl of a medium (Minimum Essential Medium Eagle Alpha Modifications, Hyclone, USA) containing 10% FBS (Fetal Bovine Serum) and 1% antibiotic-antimycotic solution (Thermo Fisher Scientific, USA) were dispensed per titanium disc. After at least 7 hours, the cells were observed to be attached to the disc surface, and the medium was additionally added to each well so that the disc would be submerged in the medium, followed by culture of the cells. On the next day, the medium was replaced with an osteogenic differentiation induction medium (Differentiation Basal Medium-Osteogenic, Lonza, USA) containing a supplement (hMSC Osteogenic SingleQuots®, Lonza, USA), and the cells were cultured for 18 days.

For 18 days after the first coating of the disc surface, the cells were cultured while replacing the medium without adding a solution containing the physiologically active substance. On day 18 of culture, the medium was removed, and the cells were stained with 2% Alizarin red S (Sigma-Aldrich, USA) solution. When the cells were mineralized to produce a mineral, the cells were stained red. Then, the cells were incubated with 10% cetylpyridinium chloride (Sigma-Aldrich, USA) at room temperature for 2 hours, and the absorbance at 570 nm was measured.

Figure 8:
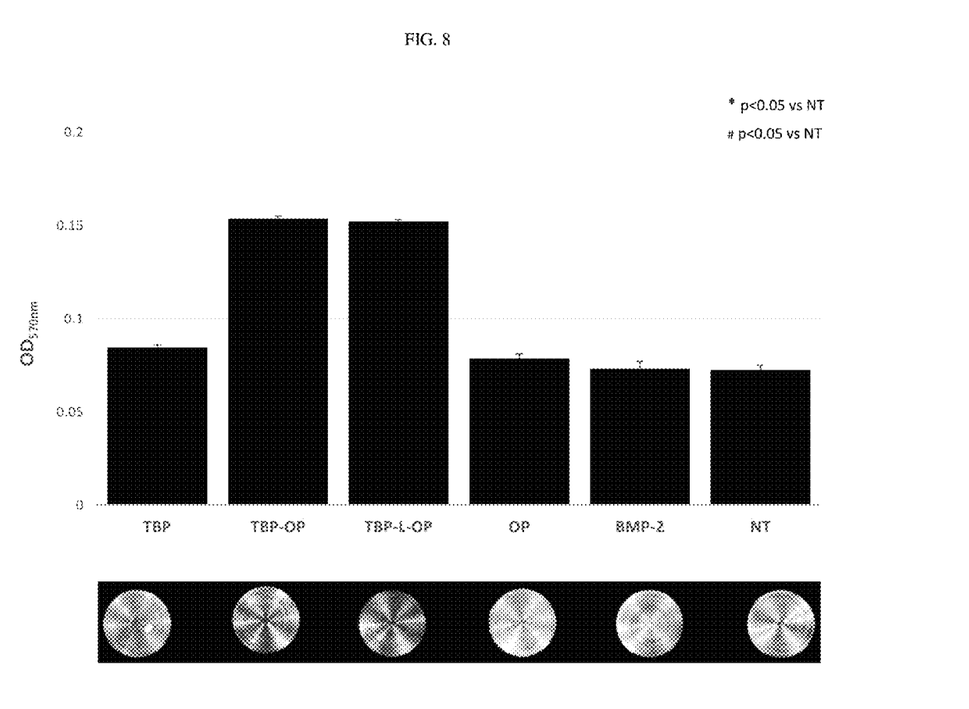
FIG. 8 shows the results of evaluating mineralization of periodontal ligament stem cells (PDLSCs) for 18 days in order to examine the osteogenic differentiation-inducting activity and loading of each of a titanium-binding peptide (SEQ ID NO: 1), an osteogenic peptide (SEQ ID NO: 3 or SEQ ID NO: 4) linked to a titanium-binding peptide, and an osteogenic peptide (SEQ ID NO: 6) when these peptides are administered once.

As a result, as shown in FIG. 8, it could be visually observed that mineral production in the test group treated with the titanium binding peptide-linked osteogenic peptide (Comparative Example 3; SEQ ID NO: 3) and the test group treated with the osteogenic peptide linked to the titanium binding peptide by the linker (Comparative Example 4; SEQ ID NO: 4) actively occurred. Furthermore, the results of measurement of the absorbance demonstrated that the test groups treated with the osteogenic peptide linked to the titanium binding peptide showed mineralization-inducing activity. The results of analysis of statistical significance indicated that there was a statistically significant difference between the NT (negative control) group and the test group treated with the titanium binding peptide-linked osteogenic peptide (Comparative Example 3; SEQ ID NO: 3) and between the NT group and the test group treated with the osteogenic peptide linked to the titanium binding peptide by the linker (Comparative Example 4; SEQ ID NO: 4) ($p<0.05$). Furthermore, the results of the t-test indicated that there was no statistically significant difference between a negative control group and the test group treated with the titanium binding peptide alone (SEQ ID NO: 1), and between the test group treated with the titanium binding peptide-linked osteogenic peptide (Comparative Example 3; SEQ ID NO: 3) and the test group treated with the osteogenic peptide linked to the titanium binding peptide by the linker (Comparative Example 4; SEQ ID NO: 4) ($p>0.05$). In addition, the results of one-way ANOVA indicated that there was no statistically significant difference between the negative control group, the control group treated with BMP-2, and the test group treated with the bond-regenerating peptide (Comparative Example 5; SEQ ID NO: 6) alone ($p>0.05$).

The results as described above suggest that, only in the presence of the titanium-binding peptide (TBP) of Example 1, a physiologically active substance can be attached securely to the surface of titanium discs or implants and can maintain its activity for a long period of time, whereas in the absence of the titanium-binding peptide, a physiologically active substance is detached from the surface of titanium discs or implants and cannot exhibit its activity.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The titanium-binding peptide according to the present invention is fixed securely to the titanium surface so that the activity of a physiologically active substance linked to the peptide can be stably maintained over a long period of time. Thus, the peptide can be effectively used for surgical regeneration therapy.

The invention claimed is:

1. A titanium-binding peptide represented by the amino acid sequence of SLNYTGHRPVVH (SEQ ID NO: 1).

2. A peptide conjugate comprising a physiologically active peptide or protein linked to the titanium-binding peptide of claim 1.

3. The peptide conjugate of claim 2, wherein the physiologically active peptide is selected from the group consisting of anti-inflammatory, anti-microbial, cell adhesion, bone tissue regeneration, and cell migration functional peptides.

4. The peptide conjugate of claim 2, wherein the physiologically active protein is selected from the group consisting of a tissue regeneration factor, a tissue growth factor, an intracellular transcription factor, an extracellular matrix protein, and an anti-inflammatory protein.

5. The peptide conjugate of claim 2, wherein the peptide conjugate is represented by an amino acid sequence of SEQ ID NO: 3 or 4.

6. A biomaterial comprising the titanium-binding peptide of claim 1 or a peptide conjugate thereof, comprising a physiologically active peptide or protein linked to said titanium-binding peptide, wherein the biomaterial is any one selected from the group consisting of a titanium-coated metal, a titanium-containing metal, a titanium-coated natural polymer, a natural polymer mixed with titanium, a titanium-coated synthetic polymer, a synthetic polymer mixed with titanium, and an implant for in vivo implantation made of titanium.

7. The biomaterial of claim 6, wherein the titanium is an alloy obtained by adding 5-7 wt % of aluminum, 3-5 wt % of vanadium, 0-0.25 wt % of iron and 0-0.2 wt % of oxygen to pure titanium oxide.

8. The biomaterial of claim 6, wherein the natural polymer is any one selected from the group consisting of collagen, alginic acid, alginic acid, chondroitin sulfate, and chitosan.

9. The biomaterial of claim 6, wherein the synthetic polymer is any one selected from the group consisting of polylacticglycolic acid, poloxamer, and propylene glycol.

* * * * *

SEQUENCE LISTING

```
<160> NUMBER OF SEQ ID NOS: 11

<210> SEQ ID NO 1
<211> LENGTH: 12
<212> TYPE: PRT
<213> ORGANISM: Artificial Sequence
<220> FEATURE:
<223> OTHER INFORMATION: Titanium Binding Peptide

<400> SEQUENCE: 1

Ser Leu Asn Tyr Thr Gly His Arg Pro Val Val His
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Titanium Binding Peptide-Control(4 amino acid
      substitution from Titanium Binding Peptide)

<400> SEQUENCE: 2

Val Ser Ala Ala Gly Thr Lys Ala Ser Pro Ala Val
```

```
1               5               10
```

```
<210> SEQ ID NO 3
<211> LENGTH: 31
<212> TYPE: PRT
<213> ORGANISM: Artificial Sequence
<220> FEATURE:
<223> OTHER INFORMATION: Fusion Peptide of Titanium Binding Peptide and
      Bone Regenerative Peptide

<400> SEQUENCE: 3

Ser Leu Asn Tyr Thr Gly His Arg Pro Val Val His Gly Leu Arg Ser
1               5                   10                  15

Lys Ser Lys Lys Phe Arg Arg Pro Asp Ile Gln Tyr Pro Asp Ala
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Fusion Peptide of Titanium Binding Peptide and
      Bone Regenerative Peptide, wherein Titanium Biding Peptide and
      Bone Regereative Peptide are connected by a linker.

<400> SEQUENCE: 4

Ser Leu Asn Tyr Thr Gly His Arg Pro Val Val His Gly Leu Arg Ser
1               5                   10                  15

Lys Ser Lys Lys Phe Arg Arg Pro Asp Ile Gln Tyr Pro Asp Ala
            20                  25                  30

<210> SEQ ID NO 5
<211> LENGTH: 12
<212> TYPE: PRT
<213> ORGANISM: Artificial Sequence
<220> FEATURE:
<223> OTHER INFORMATION: Zirconia Binding Peptide

<400> SEQUENCE: 5

Val Ser Pro Phe Gly Thr Lys Trp Ser Pro Phe Val
1               5                   10

<210> SEQ ID NO 6
<211> LENGTH: 19
<212> TYPE: PRT
<213> ORGANISM: Artificial Sequence
<220> FEATURE:
<223> OTHER INFORMATION: Bone Regenerative Peptide

<400> SEQUENCE: 6

Gly Leu Arg Ser Lys Ser Lys Lys Phe Arg Arg Pro Asp Ile Gln Tyr
1               5                   10                  15

Pro Asp Ala

<210> SEQ ID NO 7
<211> LENGTH: 8
<212> TYPE: PRT
<213> ORGANISM: Artificial Sequence
<220> FEATURE:
<223> OTHER INFORMATION: Clone 2/ 8 peptide

<400> SEQUENCE: 7

His Ser Tyr Lys His Leu Phe Ala
1               5
```

```
<210> SEQ ID NO 8
<211> LENGTH: 12
<212> TYPE: PRT
<213> ORGANISM: Artificial Sequence
<220> FEATURE:
<223> OTHER INFORMATION: Clone 16 peptide

<400> SEQUENCE: 8

Asn Ile Asn Phe Ser Phe Gly Pro Val Thr His Ile
1               5                   10

<210> SEQ ID NO 9
<211> LENGTH: 36
<212> TYPE: DNA
<213> ORGANISM: Artificial Sequence
<220> FEATURE:
<223> OTHER INFORMATION: Clone 1, 3-7, 9-15, and 17 DNA sequence

<400> SEQUENCE: 9
tctcttaatt atacggggca tcgtccggtt gtgcat                                 36

<210> SEQ ID NO 10
<211> LENGTH: 24
<212> TYPE: DNA
<213> ORGANISM: Artificial Sequence
<220> FEATURE:
<223> OTHER INFORMATION: Clone 2, 8 DNA sequence

<400> SEQUENCE: 10
catagttata agcatctttt tgct                                              24

<210> SEQ ID NO 11
<211> LENGTH: 36
<212> TYPE: DNA
<213> ORGANISM: Artificial Sequence
<220> FEATURE:
<223> OTHER INFORMATION: Clone 16 DNA sequence

<400> SEQUENCE: 11
aatattaatt tttcgtttgg tccggtgact catatt                                 36
```